(12) United States Patent
Fitz

(10) Patent No.: US 6,547,766 B1
(45) Date of Patent: Apr. 15, 2003

(54) CATHETER WITH VARIABLE DIMENSION GUIDE WIRE LUMEN

(75) Inventor: Matthew J. Fitz, Santa Clara, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/569,208

(22) Filed: May 11, 2000

(51) Int. Cl.[7] ................................................. A61M 5/14
(52) U.S. Cl. ...................................................... 604/264
(58) Field of Search ........................... 604/264, 39, 43, 604/159, 168.01, 265, 167.02, 103.1

(56) References Cited

U.S. PATENT DOCUMENTS 5,066,285 A * 11/1991 Hillstead .................... 600/585
5,300,032 A * 4/1994 Hibbs et al. ............. 604/164.1

* cited by examiner

*Primary Examiner*—Teresa Walberg
*Assistant Examiner*—Vinod D Patel
(74) *Attorney, Agent, or Firm*—Fulwider Patton Lee & Utecht, LLP

(57) ABSTRACT

An intraluminal catheter customizable to accept various diameter guide wires is disclosed. The catheter has a large bore lumen for receiving a large diameter guide wire, and alternatively, for receiving an adaptor tube therein. The adaptor tube includes a small guide wire lumen for accepting smaller guide wires of various diameters. With the adaptor tube telescopically disposed within the large bore catheter, the distal end of the adaptor tube optionally projects beyond the distal end of the large bore catheter. To minimize any onset of snow plowing effects at the distal end of the catheter, the outside diameter of the adaptor tube is made to closely conform to the inside diameter of the large bore catheter. An end cap is tightly fitted to the proximal end of the large bore catheter. The end cap secures the large bore catheter to the proximal end of the adaptor tube by the latter's interference fit with a concentric stub tube on the end cap.

20 Claims, 2 Drawing Sheets

CATHETER WITH VARIABLE DIMENSION GUIDE WIRE LUMEN

BACKGROUND OF THE INVENTION

The present invention relates to a catheter for insertion into bodily vessels and an accompanying method. More particularly, the invention relates to a method and an apparatus for catheter insertion over guide wires of different diameters.

In many instances of patient treatment, it is necessary to implant a vascular prosthesis (stent) into the human vasculature in an effort to maintain the patency of the vessel. Stents are typically implanted by use of a catheter which is inserted into the human vasculature at an easily accessible location and then advanced through the vasculature to the deployment site.

One type of catheter used to deliver a stent to the target location is a coaxial, over the wire delivery catheter. Typically, such a delivery catheter is formed with an inner guide wire lumen which is configured to be passed over a guide wire of a particular size. Though it is possible to utilize a catheter having an inner lumen designed for use with a large diameter guide wire with a smaller diameter guide wire, the result is not desirable.

The first problem with using a catheter having an inner lumen designed for use with a large diameter guide wire on a small diameter guide wire relates to what is known as the "snow plow" effect. The "snow plow" effect occurs due to the gap formed between the inner diameter of the catheter inner lumen and the outer diameter of the small diameter guide wire. As a result, the leading edge of the catheter can be displaced eccentrically to one side relative to the wire thus creating somewhat of a scoop which plows forward upon telescoping of the catheter over the guide wire. Often this causes the leading edge of the catheter to scrape along the delicate inner surfaces of the blood vessel. This "snow plow" effect sometimes results in unwanted separation of tissue or plaque as the catheter is maneuvered into position.

The second problem with using a catheter having an inner lumen designed for use with a large diameter guide wire on a small diameter guide wire relates to user control over the movement of the catheter. Because the leading edge of a catheter can shift laterally a considerable distance on a small diameter guide wire, precise control is lost over the distal extremity of the catheter. Such lateral shifting of the catheter on the guide wire can contribute to binding between the catheter and the guide wire, and also may cause irregular frictional resistance to relative longitudinal movement whereby user control is diminished.

One proposed solution to the problem has been to create an array of catheters which differ only in their guide wire lumen diameters to accommodate the various guide wire diameters. However, this presents another problem because the manufacturer is burdened with the task of making separate catheter designs and requiring that customers stock each size. Additionally, customers are burdened with the inconvenience and expense of stocking a multitude of different catheters for different sized guide wires.

A catheter and method of implementation are therefore required that overcome the shortcomings inherent in previously known devices. More specifically, a safe, easily manipulable, and cost-effective catheter is needed that provides the requisite flexibility to be compatible with guide wires of different diameters.

SUMMARY OF THE INVENTION

The present invention provides for a catheter which substantially increases safety over prior art catheters and a corresponding method of implementing said catheter. Moreover, the catheter of the present invention is relatively inexpensive to manufacture, trouble-free, reliable, and easy to use. Further, the method provided herein provides a safe and innovative approach to implementing the catheter in a vessel.

As mentioned above, one type of catheter used to deliver the stent to the target location is a coaxial, over the wire delivery catheter. Typically, such a delivery catheter is formed with an inner guide wire lumen designed to be compatible with a standard size guide wire. Standard size guide wires are typically available in four different sizes. Though it is possible to use a catheter having an inner lumen designed for use with a large diameter guide wire with a smaller diameter guide wire, as discussed above, the result is not desirable. Although the present invention catheter system is described in connection with stent delivery catheters, it can be easily adapted to vascular catheters, and to virtually any catheter for access to any bodily conduit.

The present invention substantially improves safety and user manipulability by means of its multi-guide wire compatibility. More specifically, the catheter of the present invention is adjustable to conform closely with a plurality of different diameter guide wires. The close conformance of the catheter with the guide wire ensures a minimal gap between the outer diameter of the guide wire and the catheter inner lumen diameter. This minimized gap allows for enhanced control of relative movement of the catheter and alleviates the "snow plow" effect.

Any shifting and flexing of the guide wire while in the catheter inner lumen as allowed by a gap can create a binding effect whereby the device loses its coaxial characteristics thereby making it difficult for the user to accurately control. The catheter of the present invention eliminates such a gap and alleviates the above-mentioned detrimental effects because the user can select the catheter construction to be compatible with the diameter of the guide wire employed. Specifically, the tight conformance between the customized catheter guide wire lumen and the guide wire minimizes the detrimental gap.

The minimized gap between the guide wire and the interior diameter at the distal end of the catheter directly relates to the high degree of safety and user manipulability of the catheter. Minimization of the gap contributes to enhanced control of the catheter as it is advanced along the guide wire defining the path through the vessel lumens of the human vasculature.

In regards to expense, the present invention can reduce costs to the end user because of its multi-guide wire capability. Compared to conventional catheters, which are only appropriately used for one size guide wire, the catheter of the present invention can be used safely with a variety of differently sized guide wires, thus reducing the number of catheters the end users must stock. By reducing the numbers in stock, the costs associated with using the present invention catheter is significantly less than that of conventional catheters.

In order to be compatible with a plurality of guide wires, the catheter of the present invention can be formed in a multi-piece fashion. For example, a preferred embodiment of the present invention is formed from three pieces. In this embodiment, the present invention includes a catheter, an adaptor tube, and a lock.

The catheter is formed similarly to a conventional over-the-wire catheter. In this respect, the catheter of the preferred embodiment includes an inner guide wire lumen having an inner diameter sized to accommodate a larger diameter guide wire in close conformance. The inner diameter of the catheter inner guide wire lumen of the preferred embodiment is approximately 0.035 inch. With this relatively large inner diameter, the catheter is capable of accepting guide wires with diameters of up to 0.035 inch, for example.

It is not, however, optimally sized for use with smaller diameter guide wires. Thus, if a smaller diameter guide wire is used, an eccentric gap is created between a smaller diameter guide wire and the inner diameter of the catheter inner lumen resulting in the "snow plow" effect and additionally causing binding between the catheter inner lumen and guide wire, which results in restricted longitudinal shifting and decreased control as mentioned above.

To avoid any potentially adverse effects when using guide wires smaller than 0.035 inch, a preferred embodiment of the present invention includes an adaptor tube to be placed inside the catheter. The inner diameter of this adaptor tube is sized to receive, in close conformance, a smaller diameter guide wire. In this regard, a plurality of adaptor tubes can be kept on hand to accommodate a variety of guide wires of varying diameters. With this option, the present invention customizable catheter can be used with a variety of different guide wires.

In order to secure the adaptor tube to the catheter, close conformance between the two is helpful. Additionally, end cap locking means are provided to secure the adaptor tube to the catheter. The end cap locking means may be any one of a number of conventional couplings or locks, such as threaded brakes, snap fittings, press fittings, or bayonet style fittings.

During use, a patient's vascular system may be accessed, via a convenient location such as the femoral artery, with a large or small diameter guide wire in accordance with well known and established procedures. Thereafter, the physician selects the appropriate catheter with or without an adaptor tube to be telescoped over the guide wire to maintain a guiding relationship at the distal extremity. The physician then slides the appropriately sized catheter over the guide wire to the desired location within the human vasculature.

As seen by the preferred embodiment mentioned above, the catheter of the present invention is relatively inexpensive to manufacture along with being safe and controllable because of its variable, customizable construction.

Other features and advantages of the invention will become apparent from the following detailed description, taken in conjunction with the accompanying drawings, which illustrate, by way of example, the principles of the invention.

BRIEF DESCRIPTION OF THE DRAWINGS

FIG. 3 is a side elevational view, partially in section of the present invention catheter shown in FIGS. 1 and 2a.

DETAILED DESCRIPTION OF THE PREFERRED EMBODIMENTS

Figure 1:
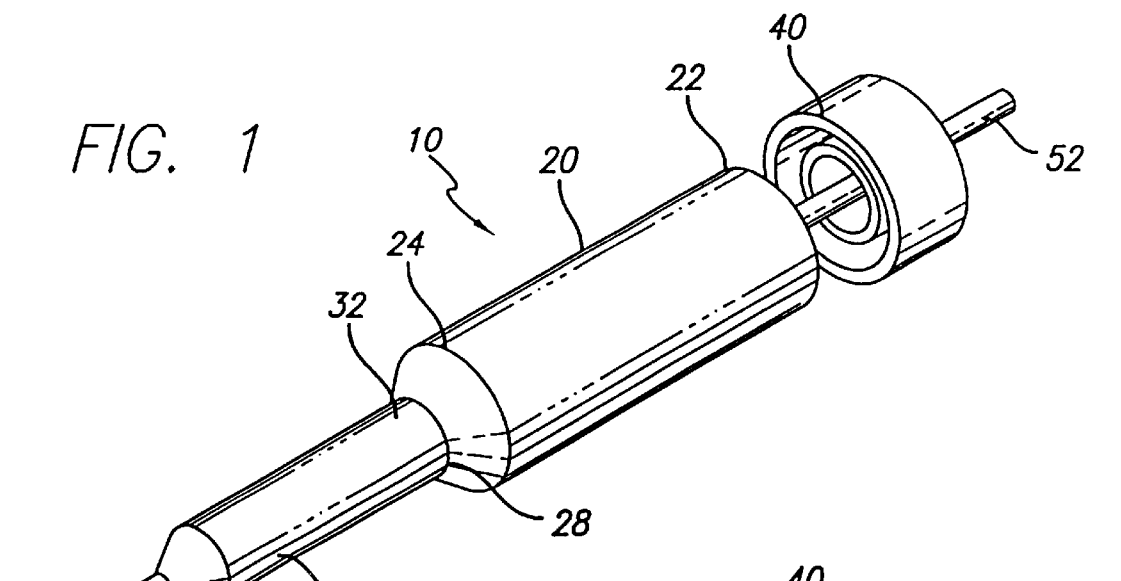
FIG. 1 is a perspective view of a preferred embodiment of the present invention catheter loosely assembled to show a small diameter guide wire, an adaptor tube, a large bore catheter, and an end cap.

As shown in the drawings for purposes of illustration, the apparatus of the invention is directed to a device preferably incorporating an intraluminal catheter, an adaptor tube, and a locking cap, for use with a large variety of guide wires having differing diameters. The present invention method applies the above-mentioned components in a configuration that functions to perform safely and controllably with a plurality of different diameter guide wires.

As mentioned above, one type of catheter used to deliver the stent to the target location is a coaxial, over-the-wire delivery catheter. Typically, such a delivery catheter is formed with an inner guide wire lumen designed to be compatible with a standard diameter guide wire which is commonly available in one of four different sizes. Though it is possible to use a catheter designed to be used with a large diameter guide wire with a smaller diameter guide wire, the result is not desirable.

Figure 2A:
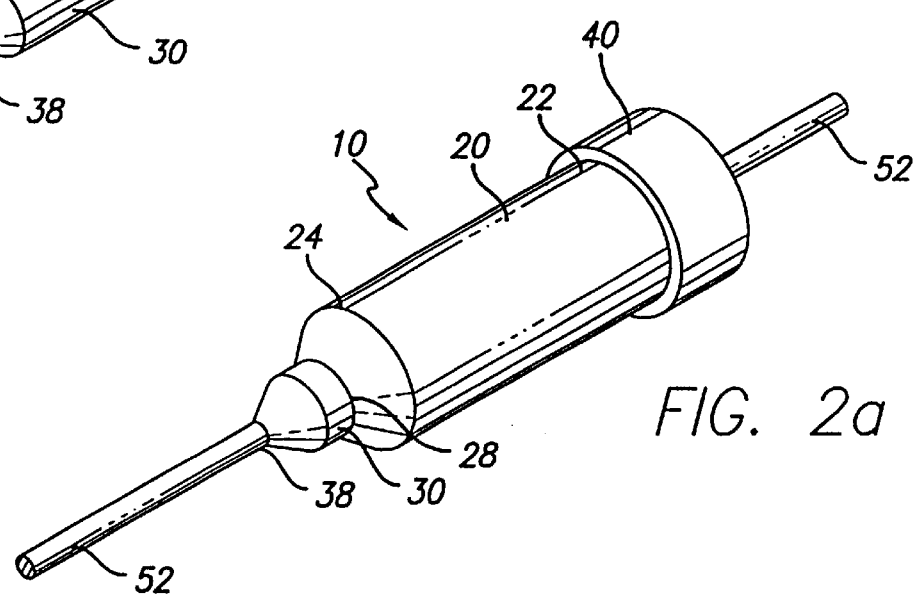
FIG. 2a is a perspective view of catheter shown in FIG. 1 with the component parts assembled together over the small diameter guide wire.
Figure 2B:
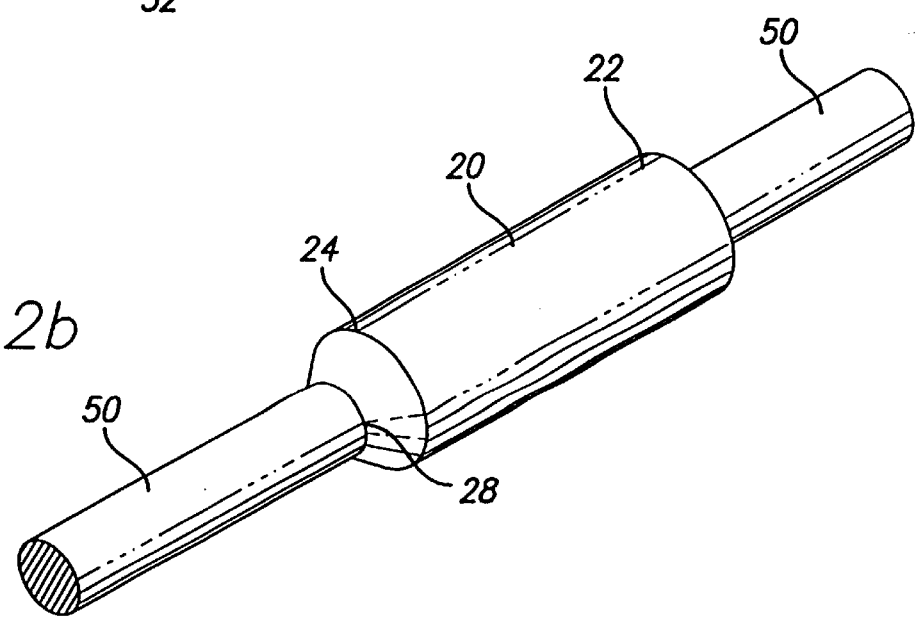
FIG. 2b is a perspective view of the large bore catheter of FIG. 1 disposed over a large diameter guide wire.

Referring now to the drawings, in which like numerals indicate like elements generally, a preferred embodiment catheter 10 has a large bore catheter 20 of typical length with an inner lumen 26 for selective telescoping over either a large diameter guide wire 50 as shown in FIG. 2b, or an adaptor tube 30 to be locked in place by a locking end cap 40, as shown in FIGS. 1 and 2a. In this second instance as seen in FIGS. 1, 2a, and 3, the adapter tube 30 has an inner lumen 36 which is designed to conform to a small diameter guide wire 52.

In the exemplary embodiments best seen in FIGS. 2a and 2b, the large bore catheter 20 can accommodate either a large guide wire 50 or an adaptor tube 30. The large bore catheter 20 has a proximal end 22, a distal end 24, a distal end port 28 and an inner lumen 26 sized to receive either the large diameter guide wire 50 or the adaptor tube 30.

Referring to FIG. 2b, when the large diameter guide wire 50 is used, the catheter 20 is sized so that its inner lumen 26 can accommodate the large diameter guide wire 50. More precisely, the diameter of the large bore catheter inner lumen 26 is sized so as to receive the large diameter guide wire 50 in close conformance to eliminate or minimize any gap between the outside diameter of the large diameter guide wire 50 and the inside diameter of the large bore catheter inner lumen 26, thereby reducing any possible "snow-plow" effect that could damage the inner vessel walls of the human vasculature. Additionally, this close conformance between the guide wire 50 and the inner lumen 26 minimizes any binding between the two, thereby permitting superior physician control of the apparatus. For femoral access in coronary procedures, such an exemplary embodiment of the present invention catheter may be configured to receive, for instance, a 0.038 inch or 0.035 inch diameter guide wire and have a length on the order of 90 cm. Such a catheter may be constructed of any conventional materials well known to those skilled in the art.

Figure 3:
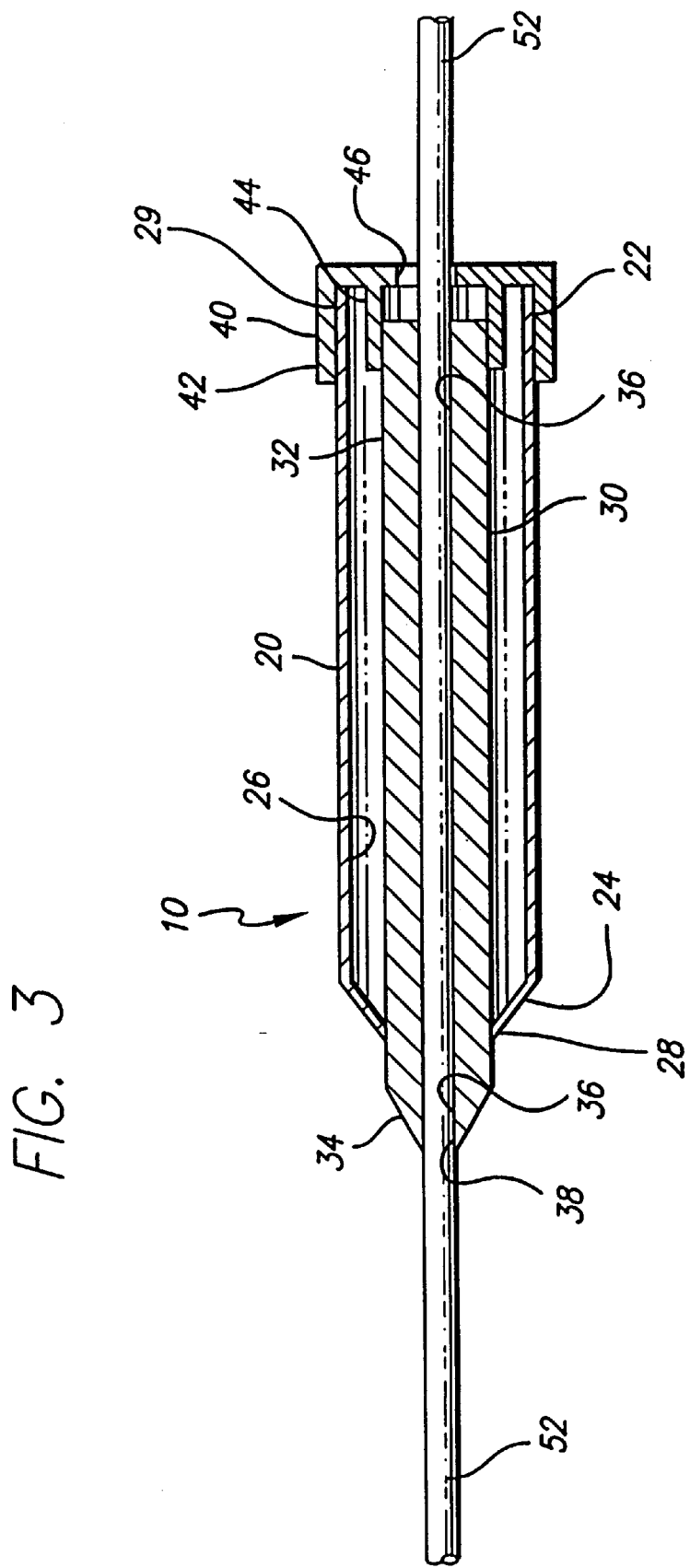

Referring to the cross-sectional view of FIG. 3, the large bore catheter inner lumen 26 is configured to accommodate either the large diameter guide wire 50 or the adaptor tube 30. Like the large bore catheter 20, the adaptor tube 30 includes an inner lumen 36 for receiving a small diameter guide wire 52 in a guiding relationship. When the small diameter guide wire 52 is used, the catheter 10 preferably includes the large bore catheter 20, the adaptor tube 30 held therein, and an end cap 40, all assembled into a single unit. This is best seen in FIGS. 2a and 3. Thus, one function of the end cap 40 is to act as a locking means to tightly secure the component parts of the catheter 10 together. To improve performance, the walls of the large bore catheter inner lumen 26 and the exterior of the adaptor tube 20 may optionally be covered with a layer of biocompatible, lubricious material such as TEFLON® or HDPE to enhance relative sliding motion of the contiguous parts.

The outside diameter of the adaptor tube 30 is designed so that the adapter tube 30 may be easily telescoped into the large bore catheter inner lumen 26 while maintaining the adapter tube 30 in close conformity therein. The closeness of the fit again eliminates, or at least minimizes, the possibility of the "snow plow" effect. A slight interference fit between the adaptor tube 30 and the large bore catheter inner lumen 26 is one example of this close conformity. Additionally, in the event the end cap 40 should become unfastened, this close conformance between the large bore catheter 20 and the adaptor tube 30 restricts free separation and thus limits damage to the vessel wall.

Referring to FIG. 3 again, the end cap 40 is also used to cover the proximal end 22 of the large bore catheter 20. The end cap 40 is configured to receive a guide wire therethrough, and includes a locking mechanism to lock the adaptor tube 30 to the large bore catheter 20. The locking mechanism is preferably the end cap 40 itself, which may be threaded and/or configured with wedge-shaped grippers to hold the proximal end 32 of the adaptor tube 30. The end cap 40 may alternatively be configured with a snap fitting, a press fitting, or any one of a number of different locking means known in the art. It is nonetheless important that such an end cap is capable of releasably gripping the adaptor tube 30 and the large bore catheter 20. This end cap construction ensures the versatility of the catheter for use with large and small diameter guide wires, as shown in FIGS. 2a and 2b.

The end cap 40 of FIG. 3 is one exemplary construction for securing the large bore catheter 20 to the adaptor tube 30. In this exemplary embodiment, the end cap 40 is configured with cylindrical peripheral wall 42 friction fitted over exterior wall 29 at the proximal end 22 of the large bore catheter 20. The end cap 40 has an access bore 46 to slidably receive small diameter guide wire 52 therethrough. Optional concentric interior stub tube 44 inside end cap 40 is preferably sized to form a tight friction fit with the proximal end 32 of the adapter tube 30. In various alternative embodiments, the interface between the proximal end 22 of the large bore catheter 20 and the proximal end 32 of the adaptor tube 30 may be secured by, for example and without limitation, a threaded connection, a snap fit, a press or interference fit, bayonet fitting, biased clamps, a clip, a weak adhesive, or any other mechanisms for releasably securing one tube to another known in the art.

The aforementioned interchangeability enables the physician to removably insert different adaptor tubes 30 having differently sized diameter inner lumens 36 into the present invention catheter in order to tailor the present invention catheter for different sized small diameter guide wires 52. Moreover, the end cap 40 is capable of being completely removed from the large bore catheter 20 in the event that a large diameter guide wire 50 is used. This embodiment is shown in FIG. 2b, where only the large bore catheter 20 is needed and the end cap 40 is removed.

The large bore catheter 20 may be configured so that the large bore catheter inner lumen 26 can receive any one of a number of other different large diameter wires greater than 0.035 inch. The diameter of the large bore catheter inner lumen 26 is not likely to be smaller than 0.038 inch, because the lumen must be sized to accept the adaptor tube 30 which is intended to receiving the small diameter guide wire 52. On the other hand, in various alternative embodiments, the large bore catheter inner lumen 26 may be sized smaller for 0.018/0.014 inch or 0.014/0.010 inch systems, where the two pairs of numbers represent the various guide wire diameters.

Referring to FIG. 3, the adaptor tube 30 is configured with its inner lumen 36 sized to receive small diameter guide wires 52. For instance, the size of the small diameter guide wire 52 is approximately 0.010 inch. The adaptor tube inner lumen 36 is sized to closely conform in a guiding relationship with the small diameter guide wire 52, which passes through a distal end port 38. In particular, the inside diameter of the adaptor tube inner lumen 36 is sized to receive the small diameter guide wire 52 in close conformance to eliminate or minimize any possible "snow-plow" effect at this distal end port 38.

In order to secure the adaptor tube inner lumen 36 to the end cap 40, the adapter tube inner lumen 36 at the proximal end 32 may incorporate any number of conventional securing means, including, but not limited to threaded brakes, snap fittings, press fittings, and bayonet fittings. The adaptor tube inner lumen 36 can also be configured to operate with standard 0.014 inch, 0.018 inch or 0.030 inch diameter guide wires in addition to a number of other differently sized, small diameter guide wires mentioned above.

In practice, the adaptor tube 30 may project along a segment of the large bore catheter 20 or, as in the case of the preferred embodiment, may project the full length of the large bore catheter 20, as shown in FIG. 3. For example, in a coronary operation, the large bore catheter 20 and the adapter tube 30 may have lengths of about 90 cm for access from the femoral artery. Of course, the adaptor tube 30 may be formed with a corresponding length or it may be longer than the large bore catheter 20.

In an alternative embodiment (not shown), for some applications, the adaptor tube 30 may be only about 10 to 20 cm long and may be releasably coupled to the large bore catheter 20 at its distal end 24. This coupling may optionally be a localized interference fit between the outside diameter of the adaptor tube 30 with the inner lumen of the large bore catheter 20 at the respective distal ends 34, 24. Furthermore, the coupling might be a screw thread, a weak adhesive, or other coupling mechanisms known in the art.

As seen in FIG. 1, the distal end 24 of large bore catheter 20 and the distal end 34 of the adaptor tube 30 may optionally include tapers. The angle and size of the tapers can be varied as needed to minimize "snow plowing" and trauma to the vessel wall. The taper may have differing profiles including, for example, straight, curved, stepped, bumpy, or the like.

During use, the physician may select a guide wire having any one of a number of different diameters for use in a particular location within the human vasculature. For example, the physician may select one of the standard size guide wires, such as a guide wire of 0.010, 0.014, 0.018, 0.030, 0.035 inch or up to about 0.038 inch in diameter. The large bore catheter 20 shown in FIGS. 1 and 2 is thus preferably sized to receive the maximum sized diameter guide wire, for example, a 0.038 inch guide wire. In the event such a guide wire is selected, the vascular system of the patient may be accessed by having the guide wire inserted, as by the femoral approach, for placement of a coronary stent or the like. In such instances, the catheter is typically about 90 cm to 110 cm long.

Where the large diameter guide wire 52 is used, after the large diameter guide wire has been inserted in place in the vascular system and reaching, for instance, from the femoral access site to the stenotic area in the large coronary arteries, the large bore catheter 20 may be telescoped thereto to be led to the target site for deployment of, for instance, a coronary stent.

In other instances where a small diameter guide wire 52 is necessary, an adaptor tube 30 corresponding with such smaller diameter guide wire may be inserted into the large bore catheter 20 by telescoping it through the large bore catheter inner lumen 26 so that it extends distally from the large bore catheter distal end port 28, as shown in FIGS. 2*a* and 3. In the preferred embodiment, the adaptor tube 30 extends throughout the full length of the large bore catheter 20 and is coupled thereto at the proximal end 22 of the large bore catheter 20 by end cap 40.

As mentioned above, the adaptor tube 30 preferably extends through to the proximal end 22 of large bore catheter 20 and is coupled thereto by means of the locking end cap 40. It can be seen in FIG. 3 that the connection between end cap 40 and the proximal end of large bore catheter 20 may be a tight friction fit, screw coupling, snap fit or bayonet coupling and that the coupling between end cap's interior stub tube 44 and the proximal end 32 of adaptor tube 30 may likewise be so configured. In any event, once the adaptor tube 30 is inserted and the end cap 40 is mated to establish the locking relationship between the adaptor tube 30 and the large bore catheter 20, the two structures are locked in an established longitudinal relationship. As shown in FIG. 1, the distal extremity of the adaptor tube 30 projects distally out of the distal end 24 of the large bore catheter 20. The large bore catheter distal end port 28 receives the distal end of the small diameter guide wire 52, which is passed through and directed toward the target site. Access bore 46 of the end cap 40 provides for the sliding action at the proximal end of the small diameter guide wire 52. The access bore 46 has a diameter sufficiently large to allow for some degree of maneuverability and/or torquing action of the catheter and guide wire at the target site. The large bore catheter and the adaptor tube 30 may then be manipulated about to complete the delivery cast. After stent deployment, the catheter system is retracted over the guide wire. Lastly, the delivery system and the guide wire can be removed from the patient's vasculature.

Although the present invention catheter system is described in connection with stent delivery catheters, it can be easily adapted to vascular catheters, and to virtually any catheter for access to any bodily conduit. Also, from the foregoing, it will be appreciated that the present invention is compatible with a plurality of differently sized guide wires because of its ability to be configured in a variety of useful ways. While several different embodiments of the invention have been illustrated and described, it will also be apparent that various modifications can be made without departing from the spirit and scope of the invention.

What is claimed:

1. A catheter having a variable dimension lumen to receive varying sized guide wires, comprising:
   a large bore catheter having a distal end and a proximal end, and having an inner lumen extending therethrough, wherein the inner lumen includes an inside diameter;
   an adaptor tube having a distal end and a proximal end, and having a guide wire lumen extending therethrough, wherein the adaptor tube includes an outside diameter that provides an interference fit to the inside diameter of the inner lumen of the large bore catheter;
   wherein the adaptor tube is disposed within the inner lumen of the large bore catheter; and
   an end cap engaging the proximal end of the large bore catheter and securing the proximal end of the adaptor tube thereto.

2. The catheter of claim 1, wherein the distal end of the adaptor tube projects out of the distal end of the large bore catheter.

3. The catheter of claim 1, wherein the distal end of the adaptor tube is secured to the inner lumen at the distal end of the large bore catheter.

4. The catheter of claim 1, wherein the inner lumen of the large bore catheter includes a lubricious material.

5. The catheter of claim 1, wherein the end cap includes a means for securing the adaptor tube to the large bore catheter.

6. The catheter of claim 1, wherein the end cap includes a access bore, and further includes a stub tube extending distally, and having an interference fit over the outside diameter of the adaptor tube.

7. The catheter of claim 1, wherein the adaptor tube is at least as long as the large bore catheter.

8. A catheter having a variable dimension lumen to receive varying sized guide wires, comprising:
   a large bore catheter having a distal end and a proximal end with an inner lumen extending therethrough and having an inside diameter;
   an adaptor tube having a distal end and a proximal end with an inner lumen extending therethrough, wherein the adaptor tube includes an outside diameter that provides an interference fit to the inside diameter of the inner lumen of the large bore catheter;
   wherein the adaptor tube is disposed within the inner lumen of the large bore catheter and the distal end of the adaptor tube projects out of the distal end of the large bore catheter; and
   an end cap having an access port and engaging the proximal end of the large bore catheter; and
   wherein the end cap includes a means for securing the proximal end of the adaptor tube to the proximal end of the large bore catheter tube.

9. The catheter of claim 8, wherein the catheter includes a lubricious material disposed between the adaptor tube and the large bore catheter.

10. The catheter of claim 8, wherein the means for securing includes a mechanism selected from the group consisting of a threaded connection, a snap fit, an interference fit, or a bayonet fit.

11. The catheter of claim 8, wherein the distal ends of the large bore catheter and the adaptor tube have a taper.

12. The catheter of claim 8, wherein the outside diameter of the adaptor tube has an interference fit to the inside diameter of the inner lumen of the large bore catheter.

13. The catheter of claim 8, wherein the inside diameter of the large bore catheter is at least approximately 0.010 inch.

14. A method for providing a catheter having a variable dimension lumen to receive varying sized guide wires, comprising:
   providing a large bore catheter having a distal end and a proximal end with an inner lumen extending therethrough and having an inside diameter;
   providing an adaptor tube having a distal end and a proximal end with an inner lumen extending therethrough, wherein the adaptor tube includes an outside diameter that provides an interference fit to the inside diameter of the inner lumen of the large bore catheter;
   disposing the adaptor tube within the inner lumen of the large bore catheter so that the distal end of the adaptor tube projects out of the distal end of the large bore catheter;

providing an end cap having an access port; and securing the proximal ends of the large bore catheter and the adaptor tube to the end cap.

15. The method of claim 14, wherein the method further comprises providing a lubricious material disposed between the adaptor tube and the large bore catheter.

16. The method of claim 14, wherein the method further comprises providing a means for securing the proximal ends of the large bore catheter and the adaptor tube to the end cap.

17. The method of claim 16, wherein the means for securing includes a method selected from the group comprising a threaded connection, a snap fit, an interference fit, and a bayonet fit.

18. The method of claim 14, wherein the method further comprises providing a taper to the distal ends of the large bore catheter and the adaptor tube.

19. The method of claim 14, wherein the method further comprises providing an interference fit between the outside diameter of the adaptor tube and the inside diameter of the inner lumen of the large bore catheter.

20. The method of claim 14, wherein the method further comprises providing an inside diameter of the large bore catheter that is at least approximately 0.010 inch.

* * * * *